(12) United States Patent
Yago et al.

(10) Patent No.: US 7,244,439 B2
(45) Date of Patent: Jul. 17, 2007

(54) COSMETIC COMPOSITION

(75) Inventors: Yuko Yago, Tokyo (JP); Keisuke Nakao, Tokyo (JP); Ryuji Hasegawa, Tokyo (JP); Noboru Nagatani, Tokyo (JP); Keiichi Fukuda, Tokyo (JP); Naoki Nojiri, Wakayama (JP); Hidetake Nakamura, Wakayama (JP); Hideaki Kubo, Wakayama (JP)

(73) Assignee: Kao Corporation, Tokyo (JP)

( * ) Notice: Subject to any disclaimer, the term of this patent is extended or adjusted under 35 U.S.C. 154(b) by 748 days.

(21) Appl. No.: 10/410,237

(22) Filed: Apr. 10, 2003

(65) Prior Publication Data

US 2004/0001869 A1 Jan. 1, 2004

(30) Foreign Application Priority Data

| Apr. 10, 2002 | (JP) | ............................. 2002-107360 |
| Apr. 10, 2002 | (JP) | ............................. 2002-107361 |
| Apr. 10, 2002 | (JP) | ............................. 2002-107362 |
| Apr. 10, 2002 | (JP) | ............................. 2002-107363 |
| Apr. 10, 2002 | (JP) | ............................. 2002-107364 |
| Apr. 10, 2002 | (JP) | ............................. 2002-107365 |

(51) Int. Cl.
*A61K 6/00* (2006.01)
*A61K 9/14* (2006.01)
*A61K 9/16* (2006.01)

(52) U.S. Cl. ........................ 424/401; 424/489; 424/490

(58) Field of Classification Search .................. 424/401
See application file for complete search history.

(56) References Cited

U.S. PATENT DOCUMENTS 5,789,027 A 8/1998 Watkins et al.
6,113,682 A * 9/2000 Shin et al.

FOREIGN PATENT DOCUMENTS

| EP | 1 053 741 A2 | * 11/2000 |
| EP | 1053741 A1 | 11/2000 |
| EP | 1 116 753 A2 | * 7/2001 |
| EP | 1116753 A2 | 7/2001 |
| FR | 2795949 | 1/2001 |
| JP | 64-63035 A | 3/1989 |
| JP | 3-181411 | * 8/1991 |
| JP | 3-181411 A | 8/1991 |
| JP | 2000-72622 A | 3/2000 |
| JP | 2000128737 A | 5/2000 |

OTHER PUBLICATIONS

Schlossman et al., The Chemistry and Manufacture of Cosmetics, vol. 2, 3rd Edition, p. 601-627, (2000).
Glebov et al., Industrial & Engineering Chemistry Research, vol. 40, No. 19, pp. 4058-4068, (2001).

* cited by examiner

*Primary Examiner*—Humera N. Sheikh
(74) *Attorney, Agent, or Firm*—Birch, Stewart, Kolasch & Birch, LLP

(57) ABSTRACT

A cosmetic composition having excellent application feeling and transparency while maintaining covering power which includes (a) composite particles obtained by allowing at least two kinds of particles having different shapes and particle diameters to contact with at least one polymer compound selected from the group consisting of fluorinated polymer compounds, silicone polymer compounds, and mixture thereof, in the presence of supercritical carbon dioxide, and (b) a cosmetic component.

9 Claims, 1 Drawing Sheet

COSMETIC COMPOSITION

FIELD OF THE INVENTION

The present invention relates to cosmetic compositions containing composite particles.

BACKGROUND OF THE INVENTION

Many cosmetic compositions have been developed in response to various needs for cosmetics. Surface treatment and complexing of cosmetic powders are among them. For example, a cosmetic powder prepared by coating the powder with silicone or organic compounds to make them water repellent and oil repellent has been widely used as a cosmetic.

However, a cosmetic powder prepared merely by coating one kind of powder with organic compounds is not considered to have sufficient makeup effect when blended into cosmetics. Various method for preparing a composite powder comprising at least two kinds of powders and polymer compounds also has been investigated.

JP-A 64-63035 proposes a powder comprising pigments on the circumferential face of spherical particles and the like, which is encapsulated with a polymer layer, in order to prevent luster and color saturation of the pigments from lowering.

JP-A 03-181411 discloses a cosmetic powder in which pigments are adhered on the surface of inorganic particles with an adhesive, and describes that a cosmetic composition containing such powder is effective for masking wrinkles.

Further, JP-A 2000-72622 describes a particle in which a first inorganic particle is coated with a second inorganic particle having a mean particle diameter of 1/10 or less of the first inorganic particle using an organic polymer compound such as a polymethyl methacrylate as a coating medium. Cosmetic compositions blended with such powder have an excellent UV blocking effect.

The composite particles prepared by these general methods known in the art are readily coagulated among the particles, and the cosmetics blended with these conventional composite particles have insufficient feeling. Furthermore, the cosmetics have poor adhesive properties and extendibility when blended with other powders, for example, spherical particles, and are deficient in covering power with little shielding effects of skin roughness i.e., pores and the like.

The present invention has found that the problems as described above can be solved by using a cosmetic composition containing composite particles prepared by allowing at least two kinds of particles having different shapes and particle diameters with respect to each other to contact a specified polymer compound in the presence of supercritical carbon dioxide.

It was also found that by combining the composite particle with specified cosmetic components, for example, a spherical powder, a powder having pearlescent shade, a volatile oil, a water-soluble thickener, zinc oxide, and a flaky powder having multi-coating layers, produces a cosmetic that makes pores inconspicuous, improves glossiness, gives fresh feeling, retains the effect of the cosmetic while suppressing the oily appearance caused by time-dependent changes, gives a moist feeling with improved adhesion and no flaky feeling, has good extendibility, retains covering power and transparency, and gives an even finish.

The present invention relates to a cosmetic composition that is excellent in application feeling and provides transparency (transparent feeling) while maintaining covering power.

The present invention also relates to a cosmetic composition that can make skin roughness, i.e., pores, inconspicuous by blending a composite particle with a spherical powder.

The present invention also relates to a cosmetic composition that can improve a lustrous feeling by blending a composite particle with a powder having pearlescent shade.

The present invention also relates to a cosmetic composition that has a fresh feeling without an oily appearance caused by time-dependent changes, and can retain makeup by blending a composite particle with a volatile oil.

The present invention also relates to a cosmetic composition that when applied, has a moist feeling and good extensibility without a flaky feeling, by using a composite particle together with a water-soluble thickener.

The present invention also relates to a cosmetic composition that has covering power and transparency with good extendibility on the skin while retaining the makeup as well as achieving less color fading, by using a composite particle together with zinc oxide.

The present invention also relates to a cosmetic composition that affords a uniform makeup with a fine-textured finish, by using a composite particle together with flaky powder having multi-coated layers.

SUMMARY OF THE INVENTION

The present invention provides a cosmetic composition comprising (a) composite particles obtained by allowing at least two kinds of particles having different shapes and particle diameters with respect to each other to contact with at least one kind of polymer compound selected from the group consisting of fluorinated polymer compounds, silicone polymer compounds and mixtures thereof, in the presence of supercritical carbon dioxide and (b) a cosmetic component.

Preferably, the cosmetic component comprises at least one kind of spherical powder with a mean particle diameter of 0.001 to 30 μm.

Preferably, the cosmetic component comprises a powder having a pearlescent shade.

Preferably, the cosmetic component comprises at least one kind of volatile oil.

Preferably, the cosmetic component comprises at least one kind of water-soluble thickener.

Preferably, the cosmetic component comprises zinc oxide with a specific surface area of 10 to 100 $m^2/g$.

Preferably, the cosmetic component comprises a powder having flaky multi-coated layers prepared by sequentially coating at least two kinds of metal oxides on a flaky base material.

The present invention preferably also provides uses of the composite particles as a cosmetic composition, a cosmetic component or a cosmetic additive.

DETAILED DESCRIPTION OF THE INVENTION

[Composite Particle]

A particle having different shapes and particle diameters refers to ones having different appearances in shape and size, and the shape includes usual shapes such as spherical, flaky, needle-like, ellipsoidal, cone-shaped, columnar and hexagonal shapes as well as peculiar shapes such as polygonal, petal-like and butterfly-like shapes, and amorphous shapes.

Combinations of at least two kinds of particles (e.g., a first particle and other particles) having different shapes and particle sizes with each other as preferably used in the invention include a combination of particles having different shapes such as flaky particles and spherical particles as well as a combination of particles having the same or different shapes with different particle sizes. The combination of particles having different particle diameters is preferable, and such a combination may include a combination of the first particle and other particles having a mean particle diameter of 1/5 or less, more preferably 1/10 or less, of the mean particle diameter of the first particle. In another preferred embodiment, when three or more types of particles are used in combination, two of the particle types could be the same shape and particle diameter so long as the first particle has a different shape or particle diameter. The particle diameter as used herein refers to a mean particle diameter calculated from the particle diameter distribution measured by conventional laser diffraction/scattering methods.

In a specific preferred example of the structure of the composite particle, fine particles (other particles; hereinafter referred to as particle B) having a mean particle diameter of 1/5 of the mean particle diameter of a first particle (hereinafter referred to as particle A) are dispersed on the surface of particle A, which is a base particle, and particle A and particle B are covered with at least one kind of polymer compound (hereinafter referred to simply as polymer compound) selected from a fluorinated polymer compound, a silicone polymer compound, and mixtures thereof. In a more specific preferred example, both particle A and particle B are covered with a polymer compound, independently, and particle B may be present on the surface of particle A. The polymer compound may be present on the surface of particle A and particle B altogether.

The preferred kind of particles to be used in the present invention is roughly divided into inorganic and organic particles. Non-limiting examples of inorganic particles include natural minerals such as mica, talc, sericite and kaolin; metal oxides such as silica, glass beads, calcium oxide, titanium oxide, zinc oxide and zirconium oxide; metal salts such as barium sulfate; metal hydroxides such as aluminum hydroxide; ceramics such as hydroxylapatite and boron nitride; metal powders such as gold powder and silver powder; inorganic pigments such as yellow iron oxide, black iron oxide and red iron oxide; and sintered products thereof.

Non-limiting examples of organic particles include polyester resins; styrene resins; urethane resins; nylon resins; cellulose resins; polyamide resins; epoxy resins; phenol resins; silicone resins such as polymethylsil sesquioxane, dimethicone cross polymer, (lauryl dimethicone/PEG) cross polymer, (dimethicone/vinyldimethicone/methicone) cross polymer and cross-linked alkylpolyether modified silicone; acrylic acid resins such as polyacrylamide, alkyl polyacrylate, copolymer of acrylic acid and alkyl polymer, alkyl acrylate/acrylamide copolymer, alkyl acrylate/dimethicone copolymer, acrylic acid/alkyl acrylate (C10 to C30) copolymer, alkyl acrylate/styrene copolymer, acrylamide/alkyl acrylate/acrylic acid DMAPA/methacrylic acid methoxypolyethylene glycol copolymer, lauryl(meth)acrylate/ethyleneglycol di(meth)acrylate copolymer and methyl methacrylate/dimethyl polysiloxane copolymer; polyolefin resins such as polyethylene and polyproppylene; fluorinated resins; and amino acids such as lauroyl lysine and lauroyl taurine.

Multilayer particles such as mica coated with titanium oxide, mica coated with red iron oxide and titanium oxide, and multi-coated resins; and metal powder occluding particles such as silica occluding titanium oxide and glass flakes occluding titanium oxide are also available and prefered. The surface of these particles may be subjected to a hydrophobic treatment or hydrophilic treatment.

Preferred particles used for particle A herein include inorganic particles such as talc, mica, sericite, kaolin, zeolite, mica coated with titanium oxide, barium sulfate, zirconium oxide, glass beads and silica; and organic particles such as polyester resin, styrene resin, nylon resin, polyamide resin, epoxy resin, phenol resin, silicone resin, acrylic resin, polyolefin resin, fluorinated resin and amino acid powders.

While the mean particle diameter of particle A is not particularly restricted, it is preferably 0.1 to 500 μm, more preferably 0.5 to 200 μm, when a particle B and a polymer compound are dispersed on the surface of particle A.

Useful particle B herein include inorganic particles such as silica, zinc oxide, titanium oxide, zirconium oxide, barium sulfate, yellow iron oxide, black iron oxide, red iron oxide and silica occluding titanium oxide; resin particles such as styrene resin, acrylic resin, polyolefin resin, nylon resin, silicon resin, fluorinated resin, polyester resin, polyamide resin, epoxy resin and phenol resin; organic pigments such as red pigments 2, 104, 201, 202 and 226, orange pigments 201 and 204, yellow pigment 4, 5, 205 and 401, blue pigments 1 and 404, green pigment 3, and purple pigment 201, and chelating pigments thereof.

The mean particle diameter of particle B is 1/5 or less, more preferably 1/10 or less, and particularly 1/20 or less, of the mean particle diameter of particle A, considering that polymer B is dispersed on the surface of polymer A. In other words, the mean particle diameter of particle B is preferably 0.001 to 100 mm, more preferably 0.01 to 40 mm, and further preferably 0.01 to 10 mm, considering that polymer B is dispersed on the surface of polymer A while improving the feeling of the composite particle.

It is preferable that the polymer compound to be used in the composite particle of the invention has a small intermolecular force, and has a property that renders the polymer to be readily dissolved or dispersed in the presence of supercritical carbon dioxide.

The fluorinated polymer compounds may be any polymer compound having fluorine atoms, and the content of the fluorine atoms in the fluorinated polymer compound is preferably 9 to 80% by mass, more preferably 20 to 70% by mass, and particularly 40 to 65% by mass, considering that the polymer is easily dispersed or dissolved in the presence of supercritical carbon dioxide.

Particularly preferable fluorinated polymer compounds are (meth)acrylic ester polymers having fluoroalkyl or perfluoro groups, and (meth)acrylic ester-long chain alkyl (meth)acrylate copolymers having fluoroalkyl or perfluoro groups, considering that the polymer is easily dispersed or dissolved in the presence of supercritical carbon dioxide. Homopolymers of (meth)acrylate having perfluoroalkyl groups, polyfluoroalkyl groups or perfluoropolyether groups with a carbon number of 4 or more, and copolymers of these compounds with (meth)acrylate having alkyl groups with a carbon number of 8 to 22 are even more preferable, considering that the polymer is easily dispersed or dissolved in the presence of supercritical carbon dioxide.

The weight-average molecular weight of the fluorinated polymer compound is preferably 3,000 to 500,000, more preferably 5,000 to 300,000, considering that the polymer is easily dispersed or dissolved in the presence of supercritical carbon dioxide and is a solid at 25° C.

The silicone polymer compounds are not particularly restricted, so long as the polymer can be dissolved or dispersed in the presence of supercritical carbon dioxide or in a mixed solvent of a supercritical carbon dioxide and a co-solvent.

Dimethyl polysiloxane, cyclic dimethyl polysiloxane, methylphenyl polysiloxane, methyl hydrogenpolysilixane, cyclic methyl hydrogenpolysilixane, dimethyl siloxane, methyl(polyoxyethylene) siloxane copolymer, dimethyl siloxane, methyl(polyoxypropylene) siloxane copolymer, polyether modified silicone, methylstyryl modified silicone, alkyl modified silicone, fluorine modified silicone, a higher fatty acid ester modified silicone, higher alcohol modified silicone and silicone modified acrylic resin are preferable among the silicone polymer compounds, considering that the polymer is readily dispersed or dissolved in the presence of supercritical carbon dioxide, and is readily adsorbed on the particles.

The particularly preferable silicone polymer compounds, considering that the polymer is readily dispersed or dissolved in supercritical carbon dioxide, comprises poly(N-acylalkyleneimine) molecular chains having repeating units represented by the formula (III):

(in the formula, $R^3$ represents a hydrogen atom, an alkyl group with a carbon number of 1 to 22, a cycloalkyl group with a carbon number of 3 to 8, an aralkyl group with a carbon number of 7 to 10, or an aryl group with a carbon number of 6 to 10, and n represents 2 or 3), bonded to the terminals and/or side chains via the groups represented by the formula (I):

(in the formula, $R^1$ and $R^2$ independently represent a hydrogen atom, an alkyl group with a carbon number of 1 to 18, or an aryl group with a carbon number of 6 to 10, and $X^-$ represents a counter-ion of a quaternary ammonium ion such as halogen ions such as $Cl^-$ and $Br^-$, or sulfonic acid ester ions such as $CH_3SO_4^-$ and $CH_3CH_2SO_4^-$), or represented by the formula (II):

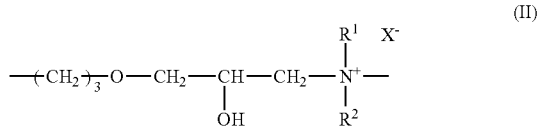

(in the formula, $R^1$, $R^2$ and $X^-$ represent the same meanings, as described above), wherein the mass ratio of the poly(N-acylalkyleneimine) molecular chain to the organopolysiloxne molecular chain is 1/50 to 50/1, and the average molecular weight is 500 to 500,000. An example of them is a poly(N-propanoylethyleneimine)/γ-aminopropyl methylsiloxane copolymer, in which $R^1$ and $R^2$ are hydrogen atoms, and $X^-$ represents $CH_3CH_2SO_4^-$ in formula (I), and $R^3$ represents $CH_2CH_3$ and n is 2 in formula (III), described in Japanese Patent Laid-open No. 7-133352.

The weight-average molecular weight of the silicone polymer compound is preferably 500 to 500,000, more preferably 1,000 to 300,000, considering that the polymer is readily dispersed or dissolved in the presence of supercritical carbon dioxide.

[Production Method of Composite Particle]

The composite particles of the invention are obtained by allowing particle A, particle B and the polymer compounds as described above to contact with each other in the presence of supercritical carbon dioxide. Supercritical carbon dioxide as used herein refers to a carbon dioxide under a pressure of supercritical pressure (7.37 MPa) or more at a supercritical temperature (304.2 K) or more, and its density rapidly changes by minute pressure changes at near the critical point. Accordingly, since the density of the vapor phase rapidly increases at a pressure slightly above the critical pressure and critical temperature, solubility of a solute rapidly increases at a pressure above the critical pressure.

For producing the composite particles, at least two kinds of particles (e.g., particle A and particle B) having different shapes and particle diameters with each other are allowed to contact polymer compounds in a vessel in the presence of supercritical carbon dioxide. A small amount of co-solvents may be used depending on the kind of polymer compound. Polar solvents are preferable as the co-solvent. Among the polar solvents, alcohols and water, which are considered to be almost nontoxic to human bodies are preferable. Methyl alcohol, ethyl alcohol and 1-propyl alcohol are preferable among the alcohols, and ethyl alcohol is most preferred.

While any combinations of the temperature and pressure are possible so long as carbon dioxide becomes supercritical, the temperature range is preferably 308 to 373 K, more preferably 313 to 353 K, considering the removal of supercritical carbon dioxide after contact and efficient reduction of the pressure. The initial pressure of supercritical carbon dioxide for starting the decrease of pressure is preferably 7.2 to 50 MPa, more preferably 10 to 40 MPa, considering the efficient reduction of the pressure of supercritical carbon dioxide.

A transparent mixture of the polymer compound and supercritical carbon dioxide is obtained by controlling the conditions such as the temperature and pressure. Such a transparent mixture is preferable for reducing the degree of coagulation of particle B (on the surface of particle A) and for forming a uniform coating layer of the polymer compound.

After allowing the polymer compound to contact at least two kinds of particles having different shapes in the presence of supercritical carbon dioxide, the composite particles of the present invention coated with the polymer compound on the surface are preferably obtained in the vessel by opening an exhaust valve provided in the vessel to reduce the pressure in the vessel (e.g., a method for obtaining the composite particles in the vessel), or the mixture after the contact is discharged out of the vessel together with carbon dioxide to preferably obtain the composite particles of the invention (e.g., a method for obtaining the composite particles outside of the vessel). Herein, reduction of the pressure of the vessel means reduction of the pressure of supercritical carbon dioxide.

In a preferred method for obtaining the composite particles in the vessel, liquid carbon dioxide is formed to readily coagulate the particle when the pressure of supercritical carbon dioxide is reduced from a pressure above the critical pressure, and when the temperature in the vessel is reduced to below the critical temperature of carbon dioxide due to adiabatic expansion of carbon dioxide. Accordingly, it is preferable to reduce the pressure of carbon dioxide in the vessel while maintaining the temperature in the vessel above the supercritical temperature of carbon dioxide in order to convert the supercritical carbon dioxide to a gaseous carbon dioxide. For this purpose, the pressure of carbon dioxide in the vessel is slowly reduced from a pressure above the supercritical temperature to the atmospheric pressure in order to reduce the pressure by isothermal expansion.

The time required for reducing the pressure in the vessel to the atmospheric pressure is preferably 2 seconds to 240 minutes, more preferably 5 seconds to 120 minutes, considering control of the particle diameter of the composite particles obtained and the thickness of the coating film of the polymer compound, and control of production of by-product particles.

In another preferred method for obtaining the composite particles outside of the vessel, the mixture is spouted and discharged out of the vessel through a nozzle. While the discharging conditions are not particularly restricted, the temperature at the inlet of the nozzle is preferably above the critical temperature of 304.2 K, and the pressure is preferably above the supercritical pressure of 7.37 MPa, considering the conditions for maintaining the supercritical fluidity.

An exhaust mechanism such as a valve may be provided for obtaining the composite particles in the vessel after removing carbon dioxide. A stirring mechanism is preferably provided in the vessel in order to dissolve or disperse at least two kinds of particles having different shapes and particle diameters with each other, and the polymer compound, in the presence of supercritical carbon dioxide. A representative example of the vessel is an autoclave and a pressure-resistant cell.

The total amount of at least two kinds of particles having different shapes and particle diameters with each other in the composite particles is preferably 20 to 99.5% by mass, more preferably 70 to 99.6% by mass, considering the handling of particles and the exhibition of characteristics of the polymer compound.

In a preferred embodiment the mean particle diameter of the composite particles obtained is preferably 0.1 to 1000 μm, more preferably 0.5 to 500 μm, and further preferably 5 to 50 μm, considering its handling as cosmetic particles.

The cosmetic composition of the invention contains the composite particles in a proportion of 0.01 to 95% by mass, preferably 0.1 to 70% by mass. The proportion is preferably 20 to 70% by mass when the cosmetic compositions are powder or solid cosmetics, and is preferably 0.01 to 30% by mass when the cosmetic compositions are liquid cosmetics.

Cosmetic Component

The cosmetic composition of the present invention contains the composite particles as well as cosmetic components generally blended in conventional cosmetics. The cosmetic component may comprise, for example, spherical powder with a mean particle diameter of 0.001 to 30 μm, a powder having, a volatile oil, a water-soluble thickener, zinc oxide with a specific surface area of 10 to 100 $m^2/g$, and flaky powders coated with a multilayer sequentially coating with at least two kinds of metal oxides on a flaky base material.

Spherical Powder

When used, the spherical powder of the invention preferably have a mean particle diameter of 0.001 to 30 mm, and particularly have spherical particles of 0.1 to 20 mm. The preferred spherical particles as used in the invention include approximately spherical particles except rod-like and plate-like particles. The particles may further comprise not only spherical primary particles, but also spherical coagulates and composites. While any kind of spherical powder is available so long as they are sphericaly shaped, they include inorganic particles such as alumina, silica, zirconia, titanium oxide, zinc oxide, zeolite and barium sulfate; and organic particles such as powders of polyester resins, styrene resins, urethane resins, nylon resins, urea resins, phenol resins, fluorinated resins, melamine resins, epoxy resins, polycarbonate resins, silicone resins and acrylic resins, polyolefin resins such as polyethylene and polypropylene resins, cellulose powders and silk powders. Examples of the silicone resin includes polymethyl sesquioxane, dimethicone cross polymer, (lauryldimethicone/PEG) cross polymer, (dimethicone/vinyldimethicone) cross polymer, and cross-linked alkylpolyether modified silicone. Examples of the acrylic resins include polyacrylamide, alkyl polyacrylate, alkyl acrylate copolymer, alkyl acrylate/acrylamide copolymer, alkyl acrylate/dimethicone copolmer, acrylic acid/alkyl acrylate (C10 to C30) copolymer, alkyl acrylate/styrene copolymer, acrylic amide/alkyl acrylate/acrylic acid DMAPA/methacrylic acid methoxy polyethyleneglycol copolymer, lauryl(meth)acrylate/ethyleneglycol/(meth)acrylae copolymer, and methyl methacrylate/dimethyl polysiloxane copolymer.

The spherical powder herein also include a particle complexed at least two of the above particles, e.g., inorganic and organic particles, or particles occluding a UV absorber may be available. Examples of them include sintered products of titanium oxide occluding silica, zinc oxide occluding silica, iron oxide occluding silica and aluminosilicate; spherical particles occluding titanium oxide, zinc oxide or iron oxide; spherical particles on which fine silica particles are adhered; and spherical particles having concentrically laminated multilayer of a polymer.

The spherical powder may be subjected to a surface treatment such as a hydrophobic treatment. Examples of the hydrophobic treatment include surface treatments of spherical particles with silicone, a higher fatty acid, a higher alcohol, a fatty acid ester, polyethylene, metallic soap, an amino acid, an alkylphosphate or a fluorinated compound by a conventional method. The silicone treatment and fluorinated compound treatment are particularly preferable.

One or at least two kinds of the spherical powder may be combined for use, and the blending ratio is preferably 0.5 to 50% by mass, particularly 1 to 20% by mass, considering adhesion on the skin and feeling of use.

In a preferred method for using the composite particles in combination with the spherical powder, both may be incorporated into the same cosmetic compositions, or they may be used as a combination after blending them into different cosmetic compositions.

For example, a cosmetic composition containing composite particles is used as an upper layer cosmetic composition while using a cosmetic composition containing the spherical powder as a base cosmetic composition, and the combination of the base and upper layer cosmetic compositions may be used as a multi-layered makeup system. Using such cosmetic system permits smooth and reliable finish to be realized with no thick makeup feeling, while maintaining a proper covering power against uneven skin color and skin roughness. The "upper layer" cosmetic composition as used herein refers to a cosmetic composition to be used on the entire face, and the base cosmetic composition as used herein refers to a cosmetic composition to be overlaid after applying the base cosmetic composition (hereinafter referred to as "base"). Examples of such products include a facing powder, foundation, finish foundation and color control powder, although name thereof is not problem herein.

The composite particles are preferably contained in the upper layer cosmetic composition in a proportion of 0.05 to 98% by mass, more preferably 0.1 to 50% by mass.

While the forms of the cosmetic composition are not important herein, they include a solid face powder, loose powder, oily solid, aqueous solid (gel), emulsion and powder dispersion considering extendibility. The solid powder may be prepared by filling in a dish using an oil or water, followed by evaporating the volatile components. In a preferred embodiment, the composite particles are contained in a proportion of 20 to 70% by mass in the powder or solid cosmetics contain, and in a proportion of 0.01 to 30% by mass in the liquid cosmetics.

Examples of the base include cosmetic foundation, cosmetic base, base foundation, control color, and foundation on which a face powder is overlaid, although name thereof is not important.

The formulation of the base is preferably an emulsion, an oily solid, an oily dispersion, an aqueous dispersion, and an aqueous solid (gel).

The spherical powder are desirably blended in the base of the invention in a proportion of 0.1 to 40% by mass, particularly 1 to 20% by mass, considering matching with the upper layer cosmetic composition.

Non-limiting examples of the combination of the upper layer cosmetic composition and base include (1) finish foundation and base foundation, (2) face powder and base foundation, (3) foundation and makeup base, (4) foundation and control color, (5) face powder and makeup base, and (6) control powder and foundation.

In a preferred method of multi-layer makeup system of the invention, the base is applied on the skin followed by overlaying the upper layer cosmetic composition. The upper layer cosmetic composition may be applied after using at least two kinds of the bases, or at least two kinds of the upper layer cosmetic composition may be used on the base.

Although the base and upper layer cosmetic compositions of the invention exhibit a very excellent effect by its use together, the upper layer cosmetic composition may be used alone depending on the preference of the user. While smoothness and reliable feeling of finish may be insufficient in this case, a makeup effect may be obtained.

Powder Having Pearlescent Shade

Mica is preferably used as base materials for the powder having pearlescent shade (hereinafter referred as a pearly pigment)of the invention. Non-limiting examples of mica-based pearly pigments include titanium coated mica having a surface coated with titanium oxide, iron oxide coated mica coated with iron oxide and titanium oxide having a surface coated with iron oxide and titanium oxide, and a powder having a silica layer sandwiched between mica and a titanium dioxide layer. Pearly pigments using base materials other than mica include a pearly pigment having a titanium oxide layer on flaky silica, a pearly pigment having a titanium oxide layer on synthetic mica, and hollow titanium oxide. The pearly pigment having a coating amount of titanium oxide of 10 to 75% by weight is particularly preferable.

The mean particle diameter of the pearly pigment is preferably 1 to 100 μm, more preferably 1 to 20 μm.

A surface treatment such as a hydrophobic treatment may be applied on the pearly pigment. Non-limiting examples of the hydrophobic treatment include surface treatment with silicone, higher fatty acids, higher alcohols, fatty acid esters, polyethylene, metallic soap, amino acids, alkyl sulfonate and fluorinated compounds. The silicone treatment and fluorinated compound treatments are particularly preferable. Inorganic particles such as silica and alumina may be coated on the surface of the pearly material in a range not compromising pearlescent shade.

Examples of commercially available pearly pigments include Flamenco Super Pearl, Flamenco Orange, Flamenco Sparkle, Timiron Super, Timiron Super Silk MP-1005, Timiron Super Scene MP-1001, Timiron Star Luster MP-115, Timica Extra Large Sparkle, Flamenco Ultra Sparkle 4500, Croisone Orange, Croisone Blue, Croisone Antique Blue, Croisone Sries Flanbe, Croisone Blue Flanbe, Croisone Sparkle (Gold, Copper, Blue, Rouge), Colorona Siena, Colorona Red Gold, Colorona Red Brown, Colorona Bride Gold, Colorona Bordeaux, Colorona Imperial Red, Colorona Siena Sparkle, Timica Golden Bronze, Timicanue antique Copper, Timica Gold Sparkle, Timiron Gold Plus MP-25, Flamenco Satin Red, Flamenco Satin Violet, Flamenco Satin Blue, Flamenco Sparkle (Red, Gold, Green, Blue, Violet), Duechrome BV, Timiron Splendid, Metashine 1080RC-(B1, G1, R1, S1, Y1), and Prominence SF.

The content of the pearly pigment is preferably 0.1 to 80% by mass, more preferably 0.1 to 50% by mass, and particularly 0.1 to 40% by mass.

Volatile Oil

The volatile oil in a preferred embodiment of the invention refers to an oil that exhibits 10% or more of weight loss after allowing to stand still at room temperature after applying on a sheet of filter paper. Examples of volatile oils include low boiling point isoparaffin with a carbon number of 10 to 13, volatile silicone oils and volatile perfluoropolyether. The volatile silicone oils represented by the following formula (IV) or (V) are also preferable:

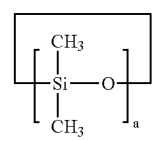

(IV)

(a = 3 ~ 6)

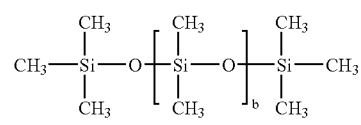

(V)

(b = 0 ~ 3)

The content of the volatile oil is preferably 1 to 50% by mass, more preferably 1 to 40% by mass, and particularly 3 to 25% by mass. The proportion of water to the volatile oil in the cosmetic compositions of the invention is preferably 1/9 to 9/1.

Water-Soluble Thickener

The water-soluble thickener in a preferred embodiment of the invention increases the viscosity of water or forms an aqueous gel when the cosmetic composition of the invention is dispersed/dissolved in water. The aqueous solution may be heated and cooled, or neutralized, for forming the gel, if necessary. The thickener may be dispersed/dissolved in an aqueous solvent that is soluble in water, e.g., ethyl alcohol when it is dispersed/dissolved in water.

Examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic hetero-polysaccharide derived form callus of plants belonging to *Polyantes* sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Carrageenan and acidic hetero-polysaccharides derived from callus of plants belonging to *Polyantes* sp. are preferable among them.

The content of the water-soluble thickener is preferably 0.01 to 20% by mass, more preferably 0.05 to 15% by mass, and particularly 0.1 to 10% by mass.

Zinc Oxide

Zinc oxide to be used in a preferred embodiment of the invention preferably has a specific surface area of 10 $m^2/g$ or more, preferably 20 $m^2/g$ or more, in view of sufficency of sebum absorption and preventing from makeup-peeling. In view of better finish, the surface area of 80 $m^2/g$ or more, particularly 100 $m^2/g$ or more is preferred. The cosmetic compositions having sufficient sebum absorbing ability while hardly causing the makeup to peel, or having fading of color over time, may be obtained by blending zinc oxide as described above.

Although it is preferable to use zinc oxide by subjecting it to a water-repelling and/or oil repelling treatment, subjecting zinc oxide to a surface treatment with a fluorine compound is not preferable since zinc oxide becomes incompatible with sebum. Zinc oxide may be blended after complexing with other particles, e.g., spherical powder which is capable of improving the feeling.

The content of zinc oxide is preferably 0.1 to 50% by mass, more preferably 1 to 20% by mass.

Flaky Powder Having Multi-Coated Layers

A referred flaky powder having multi-coated layers is prepared by sequentially coating at least two kinds of metal oxides on a flaky base material.

Preferably, the mean particle diameter of the flaky base material is 2 to 20 μm, and the thickness is 0.05 to 1 μm.

While examples of the flaky base material include talc, mica, sericite, kaolin, smectite clay minerals, synthetic mica, synthetic sericite, plate-like titanium oxide, plate-like aluminum oxide, boron nitride, barium sulfate and plate-like composite oxide of titania and silica, talc is particularly preferable among them in its feeling of use.

Examples of the metal oxide coating the flaky base material include $TiO_2$, $Fe_2O_3$, $CeO_2$, $ZnO$, $SiO_2$, $MgO$, $Al_2O_3$, $CaO$ and $ZrO_2$ and mixtures thereof. Among them, titanium oxide ($TiO_2$), aluminum oxide ($Al_2O_3$) and silica ($SiO_2$) are preferable in their refractive index, and at least one of the metal oxides is more preferably aluminumn oxide. Preferably, at least two, preferably two to three kinds of the metal oxides are selected for coating, and are coated on the flaky base material in the order from the oxides having higher refractive index to the oxide having lower refractive index. The flaky base material is preferably coated with titanium oxide and aluminum oxide in this order, or particularly coated with titanium oxide, aluminum oxide and silica in this order.

The metal oxide to be used for coating is preferably selected based on the object required for the flaky powder having multi-coated layers. For example, when the covering power is to be set higher, a metal oxide having higher refractive index, for example, titanium oxide, is preferably coated on the first layer. When the covering power is to be set lower, on the other hand, a metal oxide having intermediate refractive index, for example, aluminum oxide, is coated on the first layer. A metal oxide having lower refractive index than the first layer is desirably coated on the second layer and thereafter, in order to suppress reflection of light to retain transparency. For obtaining a more transparency, the thickness of the metal oxide coated is preferably 50 nm or less.

A flaky base material is coated with a metal oxide by conventional methods, e.g., a prescribed amount of a metal salt as a precursor of the metal oxide is hydrolyzed, or a prescribed amount of an organic metal compound is hydrolyzed in an alcoholic solvent, and then the hydrolyzed product is precipitated on the flaky base material or the material on which a coating layer has been already formed. In one embodiment, a prescribed amount of a metal salt such as titanyl sulfate is added to a dispersion of the flaky base material, and a titanium oxide coating layer with a prescribed thickness can be formed by allowing the hydrolyzed product to precipitate on the surface of the flaky base material after hydrolysis in an alkali environment.

For coating with silica as the outermost layer, a prescribed amount of an aqueous solution of alkali metal silicate salt or an organic silicone compound is added to a dispersion of the flaky base material on which a coating layer having a higher refractive index than silica has been already formed, and a polymerized silicic acid (hydrolysis condensation product) is adhered on the surface of the material already having coating layers by adding an acid or alkali, if necessary. The silica coating layer can be formed by any methods known in the art.

The thickness of the metal oxide coating layer can be determined from a geometrical surface area of the flaky base material or the material already coated with the metal oxide, or from the specific surface area measured by a nitrogen adsorption method and the density of the metal oxide to be coated. When the flaky base material is coated with titanium oxide and aluminum oxide in this order, it is preferable that the proportion of titanium oxide and aluminum oxide to be coated is 0.42 or less in $TiO_2/Al_2O_3$ mass ratio, because the difference of the surface reflection luminous energy does not become so large between a condition of the incident light angle of 45° C. and light receiving angle of 45°, and a condition of the incident light angle of 45° C. and light receiving angle of 0°, and glaring feeling is reduced. It is also preferable that the total amount of coating is 1 to 50% by mass, particularly 5 to 40% by mass, in order to maintain a good transparency while giving good feeling of use and an effect for shielding pores.

When the flaky base material is coated with titanium oxide, aluminum oxide and silica in this order, it is preferable that the proportion of coating of titanium oxide and aluminum oxide is 0.62 or less, particularly 0.42 or less, in the mass ratio of $TiO_2/Al_2O_3$, and the total amount of coating is 1 to 50% by mass, particularly 5 to 40% by mass. The amount of coating of $SiO_2$ to the powder is also preferably 0.1 to 30% by mass, particularly 0.2 to 20% by mass, considering the feeling of use (e.g., to reduce creaky feeling).

Preferably, the surface of the flaky powder having multi-coated layers is treated by the surface treatment method described in Japanese Patent Laid-open No. 11-49634 using a water-repelling/oil-repelling agent such as silicone, fluorinated compound, lecithin, amino acid, polyethylene and metallic soap for endowing the surface with water-repelling/oil-repelling properties. The preferable amount of the water-repelling/oil-repelling agent relative to the powder is 0.05 to 20% by mass, particularly 1 to 10% by mass, in order to obtain a sufficient water-repelling/oil-repelling property, and good feeling of use and light resistant property.

The content of the flaky powder having multi-coated layers is preferably 0.1 to 80% by mass, more preferably 1 to 50% by mass, and particularly 3 to 20% by mass, considering good feeling of use (extension and adhesion) and good finish of makeup (transparency and shielding pores).

Other Components

Non-limiting examples of the other components that may be blended in the present invention include hydrocarbons such as polyethylene wax, micro-crystalline wax, selecine wax and vaseline; ester oils such as oils such as diisostearyl malate and neopentylglycol caprylate; non-volatile silicone oil such as cyclomethicon and dimethicon; higher alcohols such as cetyl alcohol and oleyl alcohol; fatty acids such as stearic acid and oleic acid; a polyhydric alcohol such as glycerin and 1,3-butanediol; surfactants such as nonionic surfactant, anionic surfactant, cationic surfactant and amphoteric surfactant; lower alcohols such as ethyl alcohol; inorganic powders such as alumina, silica, zirconia, titanium oxide, zeolite and barium sulfate; coloring pigments such as organic dyes; antiseptics; UV absorbing agents such as octyl methoxycinnamate; antioxidants; pigments; moisture-retaining agents; whitening agents; circulation accelerating agents; sweat suppressing agents; pharmaceutically active components such as sterilizers and skin activating agents; and perfumes.

The cosmetic composition of the invention can be produced by conventional methods using a disper, homomixer, combination mixer, adiabatic homomixer, Henshel mixer, retro-mixer, hover mixer, planetary mixer, kneader and extruder.

The form of the cosmetic compositions available include a loose powder, press powder, cake and milky lotion. Examples of such cosmetic compositions include various cosmetics such as foundation, face powder, solid face powder, makeup base, eye-shadow, lip rouge, cheek rouge, eye brow, moisture retaining cream, UV protection cream, whitening cream, lotion, milky lotion, face washing agent and pack.

The invention provides cosmetic compositions having excellent application feeling and transparency while having good covering power.

EXAMPLE

Figure 1:
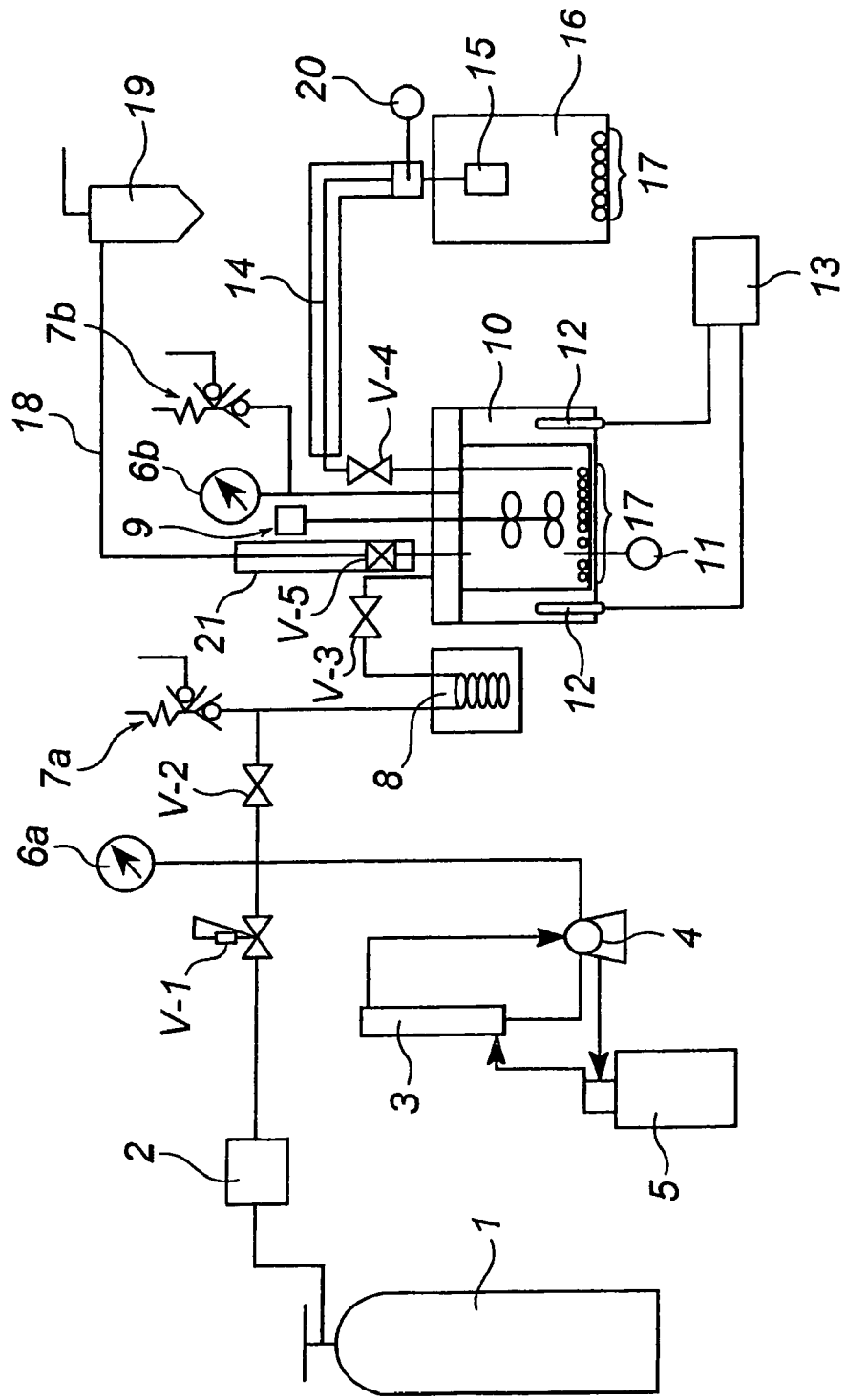
FIG. 1 is a schematic drawing of a preferred production apparatus of the composite particles used in the production examples.

Composite particles and cosmetic components to be used in the following examples are prepared. The term "%" in the examples denotes "% by mass", unless otherwise stated.

Production Example 1 of Composite Particles

<Dissolving Step>

Filled in an autoclave 10 (net volume 100 mL, made by Taiatsu Glass Co. Ltd.) in the apparatus shown in FIG. 1 were 0.36 g of poly(N-propanoyl ethyleneimine)/γ-aminopropylmethyl siloxane copolymer (copolymerization ratio 4/96 in mass ratio; weight-average molecular weight 150,000, block), 1.80 g of titanium oxide (mean particle diameter 0.05 μm, surface treatment with silicone, made by Teika Co.), and 6.00 g of talc (made by Yamaguchi Mica Co. Ltd., mean particle diameter 10 μm).

After removing dust in the carbon dioxide gas by passing the gas from a cylinder 1 through a filter 2, carbon dioxide was condensed in a condenser 3 cooled by flowing a refrigerant controlled at −5° C. with a cooler 5, and the pressure of the condensed gas was increased with a pressurizing pump 4 of which the head had been cooled. The pressure during the pressure increase was measured with a pressure gauge 6a. A safety valve 7a was provided at the downstream of the pressure gauge 6a for safety security. The pressure was controlled with a pressure retaining valve V-1.

Then carbon dioxide was passed through a pre-heater 8 by opening a valve V-2, and the gas was introduced into an autoclave 10 provided with a safety valve 7b through a valve V-3. The temperature in the autoclave 10 was regulated with a cartridge heater 12 and temperature controller 13. The temperature and pressure in the cell were adjusted to 333 K and 20 MPa, respectively, using the thermometer 11 and pressure gauge 6b, respectively, to put the gas into a supercritical carbon dioxide state. A stirrer 9 was rotated under this condition for dissolution/dispersion for 0.5 hours, thereby obtaining a mixture.

<Complexing Step>

The exhaust valve V-5 was gradually opened to discharge the gas from an exhaust line 18 (inner diameter of 2.5 mm). The pressure was decreased over 10 minutes, and composite particles were obtained. Although the temperature in the vessel decreases by an adiabatic expansion, the pressure was decreased so that the temperature in the vessel is not decreased to 313 K or less. The exhaust line was heated with the heater 21 for preventing the exhaust line from freezing.

A small amount of the composite particles leaking from the exhaust line 18 were trapped with a bug filter 19.

Production Example 2 of Composite Particles

The following complexing step was applied in place of the complexing step in the production example 1 after the dissolution step in the production example 1.

<Complexing Step>

After dissolving/dispersing the mixture for 0.5 hours by rotating the stirrer 9, the valve V-4 was opened. A mixture was obtained in a particle collecting vessel 16 from a nozzle 15 through a line previously heated with a heater 14, and the mixture was spouted to obtain spouted particles as composite particles without coagulation. The temperature immediately before the inlet of the nozzle was 313 K or more as confirmed with a thermometer 20.

Production Example 3 of Composite Particles

Composite particles 17 were produced by the same method as in production example 1, except that 0.36 g of stearyl methacrylate/2-(perfluorooctyl)ethylmethacrylate (particles with a weight-average molecular weight of 180,000 and particle diameter of 1 to 5 mm) and titanium oxide (mean particle diameter of 0.2 mm, surface silicone treatment, made by Ishihara Co.) were used in place of poly(N-propanoyl ethyleneimine)/g-aminopropyl methylsiloxane copolymer and titanium oxide (mean particle diameter of 0.05 mm, surface silicone treatment, made by Teika Co.), respectively, used in the manufacturing example 1.

Comparative Production Example 1 (Solvent Evaporation Method)

After placing 0.25 g of poly(N-propanoyl ethyleneimide)/γ-aminopropyl methylsiloxane copolymer as used in the production example 1 in a 500 mL flask, 190 g of ethyl alcohol was added, and the mixture was stirred at 25° C. to dissolve the poly(N-propanoyl ethyleneimide)/γ-aminopropyl methylsiloxane copolymer. Then, 7.5 g of talc (mean particle diameter of 10 μm, made by Yamaguchi Mica Co.Ltd.) and 2.25 g of titanium oxide (mean particle diameter of 0.05 μm, surface silicone treatment, made by Teika Co.) were added, and ethyl alcohol was evaporated off at 55° C. and 7 kPa with stirring. Many particles were adhered on the inner wall of the flask, and the composite particles 4 were obtained as coagulated particles.

Comparative Production Example 2

The composite particles 17 were produced by the same method as in the production example 1, except that only 7.80 g of talc (mean particle diameter 10 mm, made by Yamaguchi Mica Co. Ltd.) was added without adding titanium oxide used in the production example 1.

Production Example 1 of Powder Having Pearlescent Shade

Dissolved in 2000 parts of ion-exchange water was 60 parts of iron (III) sulfate nanohydrate, and the solution was adjusted to pH 2.8 with 0.1 mol/L sodium hydroxide, and 100 parts of mica titanium made by ENGELHARD company (Flamenco Satin Gold 260 M, mean particle diameter 7.9 μm, optical thickness of titanium dioxide 190 nm) was added to the aqueous solution obtained. The powder of Flamenco Satin Gold 260 M was uniformly dispersed with thorough stirring. Subsequently, the dispersion was heated with stirring to boil for 6 hours. After cooling, the dispersion was filtered, and the filtered powder was washed with water, thereby obtaining 103 parts of yellow colored mica titanium coated with yellow iron oxide. The coating ratio of yellow iron oxide on the obtained yellow-colored mica titanium was 6.67%. The mean particle diameter was 8.2 μm.

Production Example 2 of Powder Having Pearlescent Shade

Mica titanium (Flamenco Satin Red 460 M, mean particle diameter of 6.8 μm, optical thickness of titanium dioxide 260 nm) was used in place of mica titanium (Flamenco Satin Gold 260 M) of Production example 1 of powder having pearlescent shade. The dispersion was heated and stirred at boiling temperature for 6 hours. After cooling, the dispersion was filtered, the filtered powder was washed with water. The powder was baked at 800° C. for 2 hours, thereby obtaining 102 parts of red-colored mica titanium coated with red iron oxide. The coating ratio of red iron oxide on the red-colored mica titanium obtained was 6.25%, and mean particle diameter thereof was 7.3 μm.

Production Example 1 of Flaky Powder Having Multi-Coated Layers

Thoroughly dispersed by adding in 3160 g of pure water was 340 g of sericite, and 200 g of an aqueous titanyl sulfate with a concentration of 20% was added to the dispersion as titanium dioxide. The dispersion was boiled for 5 hours while stirring. The dispersion was cooled to room temperature, filtered, and the filtrate was washed with water, and then dried at 110° C., thereby obtaining sericite coated with hydrated titanium dioxide.

Thoroughly dispersed in 2680 g of pure water were 320 g of the powder, sericite coated with hydrated titanium dioxide, above, and 800 g of an aqueous aluminum chloride with a concentration of 10% as aluminum oxide and an aqueous solution of 500 g of urea in 1800 g of water were added to the dispersion with thorough stirring. The mixed dispersion was heated at 90° for 10 hours, followed by cooling to room temperature. The dispersion was filtered, and the filtrate was washed with water, dried at 110° C., and baked at 600° C. for 5 hours, thereby obtaining sericite sequentially coated with titanium oxide and aluminum oxide.

100 g of this sericite sequentially coated with titanium oxide and aluminum oxide were thoroughly dispersed by adding into 1 L of a mixed solvent of ethyl alcohol and water (7:3). Added into this dispersion was 278 g of ethyl alcohol solution of ethyl orthosilicate with a concentration of 4% as silica, and the dispersion was kept at 50° C. for about 10 hours by heating with stirring. The dispersion was filtered after cooling, and the filtrate was thoroughly washed with ethyl alcohol and pure water, thereby obtaining sericite sequentially coated with titanium oxide, aluminum oxide and silica.

Production Example 2 of Flaky Powder Having Multi-Coated Layers

Thoroughly dispersed by adding in 3132 g of pure water was 368 g of talc, and 158 g of an aqueous titanyl sulfate with a concentration of 20% as titanium dioxide was added to the dispersion. The dispersion was boiled for 5 hours while stirring. The dispersion was cooled to room temperature, filtered, and the filtrate was washed with water and dried at 110° C., thereby obtaining talc coated with hydrated titanium dioxide.

Thoroughly dispersed in 2686 g of pure water were 314 g of the powder above(talc coated with hydrated titanium dioxide), and 860 g of an aqueous aluminum chloride with a concentration of 10% as aluminum oxide and an aqueous solution of 640 g of urea in 2,000 g of water were added to the dispersion with thorough stirring. The mixed dispersion was heated at 90° for 10 hours, followed by cooling to room temperature. The dispersion was filtered, and the filtrate was washed with water, dried at 110° C., and baked at 600° C. for 5 hours, thereby obtaining talc sequentially coated with titanium oxide and aluminum oxide.

Examples 1 to 3, Comparative Examples 1 to 3 (Powder Foundation)

The powder foundations having the compositions shown in Table 1 were produced by the production method below, and were evaluated by the evaluation method 1. The results are shown in Table 1.

<Production Method>

The components (1) to (13) were mixed and pulverized by a pulverizing machine. The product was transferred to a high speed blander, and the components (14) to (19) after mixing at 80° C. were added to form a uniform mixture. The product was pulverized again, filtered, and molded by compression in a die.

TABLE 1

|  |  |  | Example | | | Comparative example | | |
| --- | --- | --- | --- | --- | --- | --- | --- | --- |
|  |  |  | 1 | 2 | 3 | 1 | 2 | 3 |
| Blend composition (%) | (1) | Composite particle in production example 1 | 50 |  |  |  |  |  |
|  | (2) | Composite particle in production example 2 |  | 50 |  |  |  |  |
|  | (3) | Composite particle in production example 3 |  |  | 50 |  |  |  |
|  | (4) | Composite particle in comparative production example 1 |  |  |  | 50 |  |  |
|  | (5) | Composite particle in comparative production example 2 |  |  |  |  |  | 50 |
|  | (6) | Talc*1 |  |  |  |  | 50 |  |
|  | (7) | Mica treated with silicone | Balance | Balance | Balance | Balance | Balance | Balance |
|  | (8) | Barium treated with florinated resin | 5 | 5 | 5 | 5 | 5 | 5 |
|  | (9) | Zinc stearate | 2 | 2 | 2 | 2 | 2 | 2 |
|  | (10) | Titanium oxide treated with silicone | 4 | 4 | 4 | 4 | 4 | 4 |
|  | (11) | Yellow iron oxide treated with silicone | 1.7 | 1.7 | 1.7 | 1.7 | 1.7 | 1.7 |
|  | (12) | Red iron oxide treated with silicone | 1.2 | 1.2 | 1.2 | 1.2 | 1.2 | 1.2 |
|  | (13) | Black iron oxide treated with silicone | 0.1 | 0.1 | 0.1 | 0.1 | 0.1 | 0.1 |
|  | (14) | Dimethyl polysiloxane (6 mm$^2$/s) | 4 | 4 | 4 | 4 | 4 | 4 |
|  | (15) | Dimethyl polysiloxane (5000 mm$^2$/s) | 0.6 | 0.6 | 0.6 | 0.6 | 0.6 | 0.6 |
|  | (16) | Squalane | 2.4 | 2.4 | 2.4 | 2.4 | 2.4 | 2.4 |
|  | (17) | Octyl methoxycinnamate | 3 | 3 | 3 | 3 | 3 | 3 |
|  | (18) | Antiseptics | Proper amount | Proper amount | Proper amount | Proper amount | Proper amount | Proper amount |
|  | (19) | Perfume | Minute amount | Minute amount | Minute amount | Minute amount | Minute amount | Minute amount |
| Evaluation of use | Adhesion on skin(adhesion) | | ⊚ | ⊚ | ○ | Δ | X | X |
|  | Extensibility on skin(extension) | | ○ | ○ | ○ | Δ | X | Δ |
|  | Application feeling | | ⊚ | ○ | ○ | ○ | X | ○ |
|  | Covering power | | ○ | ○ | ⊚ | X | Δ | X |
|  | Transparency | | ○ | ○ | ⊚ | Δ | X | Δ |
|  | Masking of freckles and wrinkles on the face | | ⊚ | ○ | ○ | X | Δ | X |
|  | Masking of pores | | ○ | ○ | ○ | X | X | X |
|  | Masking of wrinkles | | ○ | ○ | ○ | X | X | X |
|  | Retention of makeup after time lapse(4 hours) | | ○ | ○ | ⊚ | X | Δ | Δ |

Examples of the cosmetic compositions of the invention are described below.

<Evaluation Method 1>

Feeling of use on the face (adhesion and extension on the skin, application feeling, covering power, transparency, masking of blemishes and freckles on the face, masking of pores and wrinkles, retention of makeup by time-elapse) was evaluated by sensing by ten panelists based on the criteria below.

⊚: evaluated as good by 8 or more panelists
○: evaluated as good by 5 to 7 panelists
Δ: evaluated as good by 2 to 4 panelists
X: evaluated as good by only one or no panelit Examples 4 to 7, Comparative Examples 4 (Powder Foundation)

Powder foundations having the compositions shown in table 2 were produced by the following production method, and were evaluated by the evaluation method 1. The results are shown in Table 1.

<Manufacturing Method>

The components (1) to (15) were mixed and pulverized by a pulverizing machine. The product was transferred to a high speed blander, and the components (16) to (21) after mixing at 80° C. were added to form a uniform mixture. The product was pulverized again, filtered, and molded by compression in a die.

TABLE 2

|  |  | Example 4 | Example 5 | Example 6 | Example 7 | Comparative example 4 |
|---|---|---|---|---|---|---|
| Blend composition (%) | (1) Composite particle in production example 1 | 50 | 50 |  |  |  |
|  | (2) Composite particle in production example 2 |  |  | 50 |  |  |
|  | (3) Composite particle in production example 3 |  |  |  | 50 |  |
|  | (4) Composite particle in comparative production example 1 |  |  |  |  | 50 |
|  | (5) Composite particle in comparative production example 2 |  |  |  |  |  |
|  | (6) Talc*¹ |  |  |  | 50 |  |
|  | (7) Spherical silicone resin(particle diameter 5 μm)*² | 4 |  | 4 | 4 | 4 |
|  | (8) Spherical silicone resin(particle diameter 12 μm)*³ |  | 4 |  |  |  |
|  | (9) Mica treated with silicone | Balance | Balance | Balance | Balance | Balance |
|  | (10) Barium sulfate treated with florinated resin | 5 | 5 | 5 | 5 | 5 |
|  | (11) Zinc stearate | 2 | 2 | 2 | 2 | 2 |
|  | (12) Titanium oxide treated with silicone | 4 | 4 | 4 | 4 | 4 |
|  | (13) Yellow iron oxide treated with silicone | 1.7 | 1.7 | 1.7 | 1.7 | 1.7 |
|  | (14) Red iron oxide treated with silicone | 1.2 | 1.2 | 1.2 | 1.2 | 1.2 |
|  | (15) Black iron oxide treated with silicone | 0.1 | 0.1 | 0.1 | 0.1 | 0.1 |
|  | (16) Dimethyl polysiloxane (6 mm²/s) | 4 | 4 | 4 | 4 | 4 |
|  | (17) Dimethyl polysiloxane (5000 mm²/s) | 0.6 | 0.6 | 0.6 | 0.6 | 0.6 |
|  | (18) Squalane | 2.4 | 2.4 | 2.4 | 2.4 | 2.4 |
|  | (19) Octyl methoxycinnamate | 3 | 3 | 3 | 3 | 3 |
|  | (20) Antiseptics | Proper amount | Proper amount | Proper amount | Proper amount | Proper amount |
|  | (21) Perfume | Minute amount | Minute amount | Minute amount | Minute amount | Minute amount |
| Evaluation of use | Adhesion on skin(adhesion) | ◉ | ◉ | ◉ | ◉ | Δ |
|  | Extensibility on skin(extension) | ◉ | ◉ | ◉ | ◉ | Δ |
|  | Application feeling | ◉ | ◉ | ◉ | ◉ | X |
|  | Covering power | ◉ | ◉ | ◉ | ◉ | Δ |
|  | Transparency | ◉ | ◉ | ◉ | ◉ | X |
|  | Masking of freckles and wrinkles on the face | ◉ | ◉ | ◉ | ◉ | Δ |
|  | Masking of pores | ◉ | ◉ | ◉ | ◉ | X |
|  | Masking of wrinkles | ○ | ◉ | ○ | ○ | X |
|  | Retention of makeup after time lapse(4 hours) | ○ | ○ | ○ | ◉ | Δ |

(note)
*¹talc: made by Yamaguchi Mica Co. Ltd., the mean particle diameter: 10 μm
*²spherical silicone resin: Tos-pearl 145 A, made by G.E. Toshiba Silicone Co.
*³spherical silica: Sun-sphere H121 made by Dokai Chemical Co.

| Example 8 (solid face powder) <Composition> | | |
|---|---|---|
| (1) | Composite particle in production example 1 | 50.0% |
| (2) | Polymethyl methacrylate (particle diameter 0.5 μm) | 8.0% |
| (3) | Zinc stearate | 4.0% |
| (4) | Barium sulfate treated with fluorinated resin | 10.0% |
| (5) | Titanium oxide fine particle treated with fluorinated resin | 4.0% |
| (6) | Mica treated with fluorinated resin | 5.0% |
| (7) | Talc treated with fluorinated resin | balance |
| (8) | Titanium oxide treated with fluorinated resin | 0.5% |
| (9) | Red iron oxide treated with fluorinated resin | 0.1% |
| (10) | Yellow iron oxide treated with fluorinated resin | 0.1% |
| (11) | Black iron oxide treated with fluorinated resin | 0.01% |
| (12) | Liquid paraffin | 6.0% |
| (13) | Canderila wax | 0.5% |
| (14) | Antiseptics | proper amount |
| (15) | Perfume | minute amount |

| Example 9 (loose type face powder) <Composition> | | |
|---|---|---|
| (1) | Composite particle in production example 1 | 70.0% |
| (2) | Methyl polymethacrylate (particle diameter of 20 μm; MB20C made by Sekisui Chemical Co.) | 8.0% |
| (3) | Titanium oxide treated with silicone | 0.5% |

-continued

| | | | |
|---|---|---|---|
| (4) | Red iron oxide treated with silicone | 0.1% |
| (5) | Yellow iron oxide treated with silicone | 0.1% |
| (6) | Talc treated with fluorinated resin | balance |
| (7) | Silica flake occluding titanium oxide (TSG 20 made by Nihon Ita-Glass Co.) | 10.0% |
| (8) | Dimethyl polysiloxane (6 mm$^2$/s) | 1.0% |
| (9) | Antiseptics | proper amount |
| (10) | Perfume | minute amount |

Example 10 (eye shadow)
<Composition>

| | | |
|---|---|---|
| (1) | Composite particle in production example 2 | 45.0% |
| (2) | Spherical silica (Sun-sphere NP-100 made by Dokai Chemical Co.) | 10.0% |
| (3) | Zinc stearate | 2.0% |
| (4) | Barium sulfate treated with fluorinated resin | 5.0% |
| (5) | Titanium oxide fine particle treated with fluorinated resin | 4.0% |
| (6) | Mica treated with silicone | balance |
| (7) | Talc treated with silicone | 10.0% |
| (8) | Titanium oxide treated with silicone | 1.5% |
| (9) | Red iron oxide treated with silicone | 0.2% |
| (10) | Yellow iron oxide treated with silicone | 0.8% |
| (11) | Black iron oxide treated with silicone | 0.1% |
| (12) | Squalane | 5.0% |
| (13) | Dimethyl polysiloxane (6 mm$^2$/s) | 3.0% |
| (14) | Micro-crystalline wax | 0.5% |
| (15) | Antiseptics | proper amount |
| (16) | Perfume | minute amount |

Example 11 (cheek rouge)
<Composition>

| | | |
|---|---|---|
| (1) | Composite particle in production example 3 | 35.0% |
| (2) | Spherical silicone resin (Tospearl, particle diameter of 0.5 μm) | 15.0% |
| (3) | Magnesium stearate | 2.0% |
| (4) | Barium sulfate treated with fluorinated resin | 5.0% |
| (5) | Titanium oxide fine particle treated with fluorinated resin | 4.0% |
| (6) | Mica treated with fluorinated resin | balance |
| (7) | Talc treated with fluorinated resin | 10.0% |
| (8) | Titanium oxide treated with fluorinated resin | 2.2% |
| (9) | Red 226 | 0.5% |
| (10) | Yellow iron oxide treated with fluorinated resin | 0.3% |
| (11) | Black iron oxide treated with fluorinated resin | 0.1% |
| (12) | Liquid paraffin | 3.0% |
| (13) | Dimethyl polysiloxane (6 mm$^2$/s) | 3.0% |
| (14) | Micro-crystalline wax | 0.9% |

-continued

| | | |
|---|---|---|
| (15) | Antiseptics | proper amount |
| (16) | Perfume | minute amount |

The powder cosmetic compositions obtained in Examples 8 to 11 had good extensibility and adhesion on the skin with no creaky, gritty and powdery feeling, and were transparent while masking pores, freckles and wrinkles on the face. More over, the skin seems to be bright and smooth with fine finish.

Example 12 (liquid foundation)

| | | |
|---|---|---|
| (1) | Composite particle in production example 1 | 5.0% |
| (2) | Spherical silicone resin (particle diameter 5 μm) | 2.0% |
| (3) | Water | balance |
| (4) | Dimethyl polysiloxane (6 mm$^2$/s) | 10.0% |
| (5) | Dimethyl polysiloxane (5,000 mm$^2$/s) | 1.0% |
| (6) | Mica treated with silicone | 10.0% |
| (7) | Titanium oxide treated with silicone | 6.0% |
| (8) | Yellow iron oxide treated with silicone | 1.2% |
| (9) | Red iron oxide treated with silicone | 0.5% |
| (10) | Black iron oxide treated with silicone | 0.1% |
| (11) | Squarlane | 15.0% |
| (12) | Octyl methoxycinnamate | 2.0% |
| (13) | Polyether modified silicone | 0.2% |
| (14) | Glycerin | 2.0% |
| (15) | Ethyl alcohol | 5.0% |
| (16) | Antiseptics | proper amount |
| (17) | Perfume | minute amount |

Examples 13 to 16, Comparative Examples 6 and 7

The cosmetic compositions were produced by the same method as in Example 4 using the compositions in Table 3, and were evaluated by the evaluation method 2 below. The results are shown in Table 3.

<Evaluation Method 2>

Feeling of use on the face (adhesion and extension on the skin, application feeling, covering power, transparency, glossy finish, clear-cut finish without flattening, retention of makeup by time elapse) was evaluated by sensing by ten panelists based on the criteria below.

TABLE 3

| | | | Example | | | | Comparative example | |
|---|---|---|---|---|---|---|---|---|
| | | | 13 | 14 | 15 | 16 | 6 | 7 |
| Blend composition (%) | (1) | Composite particle in production example 1 | 30 | 30 | | | | |
| | (2) | Composite particle in production example 2 | | | 30 | | | |
| | (3) | Composite particle in production example 3 | | | | 30 | | |
| | (4) | Composite particle in comparative production example 1 | | | | | 30 | |
| | (5) | Composite particle in comparative production example 2 | | | | | | 30 |
| | (6) | Mica treated wiyh silicone | Balance | Balance | Balance | Balance | Balance | Balance |
| | (7) | Talc*$^1$ | | | | | | |
| | (8) | Pearly pigment 1*$^2$ | 10 | | 10 | 10 | 10 | 10 |
| | (9) | Pearly pigment 2*$^3$ | | 10 | | | 10 | |
| | (10) | Barium treated with florinated resin | 5 | 5 | 5 | 5 | 5 | 5 |

TABLE 3-continued

|  |  | Example | | | | Comparative example | |
|---|---|---|---|---|---|---|---|
|  |  | 13 | 14 | 15 | 16 | 6 | 7 |
|  | (11) Zinc stearate | 2 | 2 | 2 | 2 | 2 | 2 |
|  | (12) Titanium oxide treated with silicone | 4 | 4 | 4 | 4 | 4 | 4 |
|  | (13) Yellow iron oxide treated with silicone | 1.7 | 1.7 | 1.7 | 1.7 | 1.7 | 1.7 |
|  | (14) Red iron oxide treated with silicone | 1.2 | 1.2 | 1.2 | 1.2 | 1.2 | 1.2 |
|  | (15) Black iron oxide treated with silicone | 0.1 | 0.1 | 0.1 | 0.1 | 0.1 | 0.1 |
|  | (16) Dimethyl polysiloxane (6 mm$^2$/s) | 4 | 4 | 4 | 4 | 4 | 4 |
|  | (17) Dimethyl polysiloxane (5000 mm$^2$/s) | 0.6 | 0.6 | 0.6 | 0.6 | 0.6 | 0.6 |
|  | (18) Squarane | 2.4 | 2.4 | 2.4 | 2.4 | 2.4 | 2.4 |
|  | (19) Octyl methoxycinnamate | 3 | 3 | 3 | 3 | 3 | 3 |
|  | (20) Antiseptics | Proper amount | Proper amount | Proper amount | Proper amount | Proper amount | Proper amount |
|  | (21) Perfume | Minute amount | Minute amount | Minute amount | Minute amount | Minute amount | Minute amount |
| Evaluation of use | Adhesion on skin(adhesion) | ⊚ | ⊚ | ⊚ | ○ | X | Δ |
|  | Extensibility on skin (Extension) | ○ | ○ | ○ | ○ | X | Δ |
|  | Application feeling | ⊚ | ⊚ | ⊚ | ⊚ | X | Δ |
|  | Covering power | ⊚ | ⊚ | ⊚ | ⊚ | Δ | X |
|  | Transparency | ⊚ | ⊚ | ⊚ | ⊚ | X | Δ |
|  | Glossy finish | ⊚ | ⊚ | ⊚ | ⊚ | Δ | Δ |
|  | Clear-cut finish(without flattening) | ⊚ | ⊚ | ○ | ○ | X | X |
|  | Retention of makeup after time lapse(4 hours) | ○ | ○ | ○ | ⊚ | Δ | Δ |

⊚: evaluated as good by 8 or more panelists
○: evaluated as good by 5 to 7 panelists
Δ: evaluated as good by 2 to 4 panelists
X: evaluated as good by only one or no panelist Example 17 (foundation)
<Composition>

| | | |
|---|---|---|
| (1) | Composite particle in production example 1 | 45.0% |
| (2) | Powder having pearlescent shade (1) | 10.0 |
| (3) | Powder having pearlescent shade (2) | 2.0% |
| (4) | Sericite | 5.0% |
| (5) | Nylon powder (particle diameter 5 μm)*[1] | 4.0% |
| (6) | Zinc stearate | 3.0% |
| (7) | Talc | balance |
| (8) | Titanium oxide treated with silicone*[2] | 9.5% |
| (9) | Red iron oxide treated with silicone | 0.2% |
| (10) | Yellow iron oxide treated with silicone | 0.8% |
| (11) | Black iron oxide treated with silicone | 0.1% |
| (12) | Liquid paraffin | 5.0% |
| (13) | Dimethyl polysiloxane(6 mm$^2$/s) | 3.0% |
| (14) | Antiseptics | Proper amount |
| (15) | Perfume | Minute amount |

*[1]Torey SP-500
*[2]treated with silicone: with dimethyl polysiloxane

Examples 18 to 20, Comparative Examples 8 to 10
(Foundation)

The foundations having the compositions shown in Table 4 were produced by the following method, and the obtained foundations were evaluated by the evaluation method 3. The results are shown in Table 4.

<Production Method>

The components (1) to (6) and components (17) to (21) are mixed and pulverized. The pulverized components are added to a mixture of the components (7) to (13), and are dispersed with stirring with the disper. Components (14) to (16), (22) and (23) mixed and dissolved in a different vessel are added in small portions into the dispersion by the disper, thereby obtaining the cosmetic compositions.

<Evaluation Method 3>

Feeling of use on the face (adhesion and extensibility on the skin, fresh feeling, covering power, transparency, retained makeup, oily appearance by time lapse) was evaluated by sensing by ten panelists based on the criteria below.

TABLE 4

|  |  |  | Example | | | Comparative example | | |
|---|---|---|---|---|---|---|---|---|
|  |  |  | 18 | 19 | 20 | 8 | 9 | 10 |
| Blend composition (%) | (1) | Composite particle in production example 1 | 5 |  |  |  |  |  |
|  | (2) | Composite particle in production example 2 |  | 5 |  |  |  |  |
|  | (3) | Composite particle in production example 3 |  |  | 5 |  |  |  |
|  | (4) | Composite particle in comparative production example 1 |  |  |  |  | 5 |  |
|  | (5) | Composite particle in comparative production example 2 |  |  |  |  |  | 5 |
|  | (6) | Talc |  |  |  | 5 |  |  |
|  | (7) | Dimethyl cyclopolysiloxane*[1] | 15 | 15 | 15 | 15 | 15 | 15 |
|  | (8) | Dimethyl cyclopolysiloxane*[2] (2 mm$^2$/s) | 5 | 5 |  |  | 5 | 5 |

TABLE 4-continued

|  |  | Example | | | Comparative example | | |
|---|---|---|---|---|---|---|---|
|  |  | 18 | 19 | 20 | 8 | 9 | 10 |
|  | (9) Dimethyl cyclopolysiloxane (6 mm²/s) | 5 | 5 | 5 | 5 | 5 | 5 |
|  | (10) Dimethyl cyclopolysiloxane (5000 mm²/s) | 1 | 1 | 1 | 1 | 1 | 1 |
|  | (11) Silicone modified with fluorine*3 | 5 | 5 | 5 | 5 | 5 | 5 |
|  | (12) Silicone modified with polyether*4 | 0.2 | 0.2 | 0.2 | 0.2 | 0.2 | 0.2 |
|  | (13) Octyl methoxycinnamate | 2 | 2 | 2 | 2 | 2 | 2 |
|  | (14) Glycerin | 2 | 2 | 2 | 2 | 2 | 2 |
|  | (15) Ethanol | 5 | 5 | 5 | 5 | 5 | 5 |
|  | (16) Water | Balance | Balance | Balance | Balance | Balance | Balance |
|  | (17) Titanium oxide treated with silicone | 6 | 6 | 6 | 6 | 6 | 6 |
|  | (18) Yellow iron oxide treated with silicone | 1.2 | 1.2 | 1.2 | 1.2 | 1.2 | 1.2 |
|  | (19) Red iron oxide treated with silicone | 0.5 | 0.5 | 0.5 | 0.5 | 0.5 | 0.5 |
|  | (20) Black iron oxide treated with silicone | 0.1 | 0.1 | 0.1 | 0.1 | 0.1 | 0.1 |
|  | (21) Mica treated with silicone | 10 | 10 | 10 | 10 | 10 | 10 |
|  | (22) Antiseptic | Proper amount | Proper amount | Proper amount | Proper amount | Proper amount | Proper amount |
|  | (23) Perfume | Minute amount | Minute amount | Minute amount | Minute amount | Minute amount | Minute amount |
| Evaluation of use | Adhesion on skin(adhesion) | ⊚ | ⊚ | ⊚ | Δ | X | X |
|  | Extensibility on skin(extension) | ⊚ | ⊚ | ⊚ | Δ | X | Δ |
|  | Fresh feeling | ⊚ | ⊚ | ⊚ | ○ | X | X |
|  | Covering power | ⊚ | ⊚ | ⊚ | X | Δ | X |
|  | Transparency | ⊚ | ○ | ⊚ | Δ | X | Δ |
|  | Retention of makeup after time lapse(4 hours) | ⊚ | ⊚ | ⊚ | X | Δ | Δ |
|  | Oily appearance after time lapse(4 hours) | ○ | ○ | ⊚ | X | Δ | Δ |

⊚: evaluated as good by 8 or more panelists
○: evaluated as good by 5 to 7 panelists
Δ: evaluated as good by 2 to 4 panelists
X: evaluated as good by only one or no panelist
*1 dimethyl cyclopolysiloxane SH245 (Toray Dow Corning Co.)
*2 dimethyl polysiloxane: KF9 (Shinetsu Chemical Co.)
*3 fluorine modified silicone, perfluoroalkyl($C_{4-14}$) ethoxydimethyl silicone (mean molecular weight of 1439)
*4 polyether modified silicone, SH3775-M (Toray Dow Corning Co.)

Examples 21 to 23, Comparative Examples 11 to 13 (Foundation)

The foundations having the compositions shown in Table 5 were produced by the following method, and were evaluated by the method in the evaluation method 4. The results are shown in Table 5.

<Production Method>

The components (1) to (6) and components (17) to (21) are mixed and pulverized. The pulverized components are added to a mixture of the separately prepared components (9) to (13), and are dispersed with stirring with the disper. Components (7), (8) (14) to (16), (22) and (23) mixed and dissolved in a different vessel are added in small portions into the dispersion by the disper, thereby obtaining the cosmetic compositions.

<Evaluation Method 4>

Feeling of use by applying the sample on the face (extensibility on the skin, moist feeling, covering power, transparency, fitting of makeup) was evaluated by sensing by ten panelists based on the criteria below.

TABLE 5

|  |  |  | Example | | | Comparative example | | |
|---|---|---|---|---|---|---|---|---|
|  |  |  | 21 | 22 | 23 | 11 | 12 | 13 |
| Blend composition (%) | (1) | Composite particle in production example 1 | 5 |  |  |  |  |  |
|  | (2) | Composite particle in production example 2 |  | 5 |  |  |  |  |
|  | (3) | Composite particle in production example 3 |  |  | 5 |  |  |  |
|  | (4) | Composite particle in comparative production example 1 |  |  |  |  | 5 |  |
|  | (5) | Composite particle in comparative production example 2 |  |  |  |  |  | 5 |
|  | (6) | Talc |  |  |  | 5 |  |  |
|  | (7) | Water-soluble thickener (tubelous polysaccharide) | 3 |  | 3 | 3 | 3 | 3 |
|  | (8) | Water-soluble thickener(cattageenen) |  | 0.2 |  |  |  |  |
|  | (9) | Silicone modified with polyether*1 | 0.2 | 0.2 | 0.2 | 0.2 | 0.2 | 0.2 |
|  | (10) | Dimethyl polysiloxane (6 mm²/s) | 10 | 10 | 10 | 10 | 10 | 10 |
|  | (11) | Dimethyl polysiloxane (5000 mm²/s) | 1 | 1 | 1 | 1 | 1 | 1 |
|  | (12) | Squarlane | 15 | 15 | 15 | 15 | 15 | 15 |

TABLE 5-continued

|  |  | Example | | | Comparative example | | |
|---|---|---|---|---|---|---|---|
|  |  | 21 | 22 | 23 | 11 | 12 | 13 |
| | (13) Octyl methoxycinnamate | 2 | 2 | 2 | 2 | 2 | 2 |
| | (14) Glycerin | 2 | 2 | 2 | 2 | 2 | 2 |
| | (15) Ethanol | 5 | 5 | 5 | 5 | 5 | 5 |
| | (16) Water | Balance | Balance | Balance | Balance | Balance | Balance |
| | (17) Titanium oxide treated with silicone | 6 | 6 | 6 | 6 | 6 | 6 |
| | (18) Yellow iron oxide treated with silicone | 1.2 | 1.2 | 1.2 | 1.2 | 1.2 | 1.2 |
| | (19) Red iron oxide treated with silicone | 0.5 | 0.5 | 0.5 | 0.5 | 0.5 | 0.5 |
| | (20) Black iron oxide treated with silicone | 0.1 | 0.1 | 0.1 | 0.1 | 0.1 | 0.1 |
| | (21) Mica treated with silicone | 10 | 10 | 10 | 10 | 10 | 10 |
| | (22) Antiseptic | Proper amount | Proper amount | Proper amount | Proper amount | Proper amount | Proper amount |
| | (23) Perfume | Minute amount | Minute amount | Minute amount | Minute amount | Minute amount | Minute amount |
| Evaluation of use | Extensibility on skin(extension) | ⊚ | ⊚ | ⊚ | X | X | X |
| | Moist feeling | ⊚ | ⊚ | ⊚ | Δ | Δ | Δ |
| | Covering power | ⊚ | ⊚ | ⊚ | X | Δ | X |
| | Transparency | ⊚ | ⊚ | ⊚ | X | Δ | Δ |
| | Fitness of makeup (no peel feeling) | ⊚ | ⊚ | ⊚ | X | X | X |

⊚: evaluated as good by 8 or more panelists
○: evaluated as good by 5 to 7 panelists
Δ: evaluated as good by 2 to 4 panelists
X: evaluated as good by only one or no panelist
*[1]polyether modified silicone, SH3775-M (Toray Dow Corning Co.)

Examples 24 to 26, Comparative Examples 14 to 16 (Foundation)

The foundations having the compositions shown in Table 6 were produced by the method in Example 4. The foundations obtained were evaluated by the evaluation method 5. The results are shown in Table 6.

<Evaluation Method 5>

Feeling of use by applying the sample on the face (extensibility on the skin, no creaky feeling, covering power, transparency, retained makeup, time-dependent fading of color) was evaluated by sensing by ten panelists based on the criteria below.

TABLE 6

|  |  | Example | | | Comparative example | | |
|---|---|---|---|---|---|---|---|
|  |  | 24 | 25 | 26 | 14 | 15 | 16 |
| Blend composition (%) | (1) Composite particle in production example 1 | 40 | 40 | | | | |
| | (2) Composite particle in production example 2 | | | 40 | | | |
| | (3) Composite particle in production example 3 | | | | 40 | | |
| | (4) Composite particle in comparative production example 1 | | | | | 40 | |
| | (5) Composite particle in comparative production example 2 | | | | | | 40 |
| | (6) Mica treated with silicone | Balance | Balance | Balance | Balance | Balance | Balance |
| | (7) Talc*[1] | | | | 40 | | |
| | (8) Zinc oxide(specific surface area 50 m²/g) | 6 | 6 | 6 | 6 | 6 | 6 |
| | (9) Zinc oxide(specific surface area 4.3 m²/g) | | | | | | |
| | (10) Barium sulfate treated with fluorinated resin | | | | | | |
| | (11) Zinc stearate | 2 | 2 | 2 | 2 | 2 | 2 |
| | (12) Titanium oxide treated with silicone | 4 | 4 | 4 | 4 | 4 | 4 |
| | (13) Yellow iron oxide treated with silicone | 1.7 | 1.7 | 1.7 | 1.7 | 1.7 | 1.7 |
| | (14) Red iron oxide treated with silicone | 1.2 | 1.2 | 1.2 | 1.2 | 1.2 | 1.2 |
| | (15) Black iron oxide treated with silicone | 0.1 | 0.1 | 0.1 | 0.1 | 0.1 | 0.1 |
| | (16) Dimethyl polysiloxane (6 mm²/s) | 4 | 4 | 4 | 4 | 4 | 4 |
| | (17) Dimethyl polysiloxane (5000 mm²/s) | 0.6 | 0.6 | 0.6 | 0.6 | 0.6 | 0.6 |
| | (18) Squarlane | 2.4 | 2.4 | 2.4 | 2.4 | 2.4 | 2.4 |
| | (19) Octyl methoxycinnamate | 3 | 3 | 3 | 3 | 3 | 3 |
| | (20) Antiseptics | Proper amount | Proper amount | Proper amount | Proper amount | Proper amount | Proper amount |
| | (21) Perfume | Minute amount | Minute amount | Minute amount | Minute amount | Minute amount | Minute amount |
| Evaluation of use | Extensibity on skin(adhesion) | ⊚ | ⊚ | ⊚ | Δ | X | Δ |
| | No creaky feeling | ⊚ | ○ | ○ | Δ | X | Δ |
| | Covering powder | ⊚ | ⊚ | ⊚ | Δ | Δ | X |
| | Transparency | ⊚ | ○ | ⊚ | X | X | Δ |

TABLE 6-continued

|  | Example | | | Comparative example | | |
|---|---|---|---|---|---|---|
|  | 24 | 25 | 26 | 14 | 15 | 16 |
| Retention of makeup after time lapse(4 hours) | ◉ | ◉ | ◉ | Δ | Δ | Δ |
| Fade of color after time lapse (4 hours) | ◉ | ◉ | ◉ | X | X | X |

◉: evaluated as good by 8 or more panelists
○: evaluated as good by 5 to 7 panelists
Δ: evaluated as good by 2 to 4 panelists
X: evaluated as good by only one or no panelist
*[1]talc: mean particle diameter 10 μm, made by Yamaguchi Mica Co.

Example 27 to 30, Comparative Examples 17 to 19 (Foundation)

The foundations having the compositions shown in Table 7 were produced by the method in Example 4. The foundations obtained were evaluated by the evaluation method 6. The results are shown in Table 7.

<Evaluation Method 6>

Feeling of use by applying the sample on the face (adhesion and extensibility on the skin, application feeling, covering power, transparency, uniform and fine makeup, time-dependent retained makeup) was evaluated by sensing by ten panelists based on the criteria below.

TABLE 7

|  |  |  | Example | | | | Comparative example | | |
|---|---|---|---|---|---|---|---|---|---|
|  |  |  | 27 | 28 | 29 | 30 | 17 | 18 | 19 |
| Blend composition (%) | (1) | Composite particle in production example 1 | 45 | 45 |  |  |  |  |  |
|  | (2) | Composite particle in production example 2 |  |  | 45 |  |  |  |  |
|  | (3) | Composite particle in production example 3 |  |  |  | 45 |  |  |  |
|  | (4) | Composite particle in comparative production example 1 |  |  |  |  |  | 45 |  |
|  | (5) | Composite particle in comparative production example 2 |  |  |  |  |  |  | 45 |
|  | (6) | Mica treated with silicone | Balance | Balance | Balance | Balance | Balance | Balance |  |
|  | (7) | Talc*[1] |  |  |  |  | 45 |  |  |
|  | (8) | Zinc oxie(specific surface area 50 m²/g) | 8 |  | 8 | 8 | 8 | 8 | 8 |
|  | (9) | Zinc oxie(specific surface area 4.3 m²/g) |  | 8 |  |  |  |  |  |
|  | (10) | Barium sulfate treated with fluorinated resin | 5 | 5 | 5 | 5 | 5 | 5 | 5 |
|  | (11) | Zinc stearate | 2 | 2 | 2 | 2 | 2 | 2 | 2 |
|  | (12) | Titanium oxide treated with silicone | 4 | 4 | 4 | 4 | 4 | 4 | 4 |
|  | (13) | Yellow iron oxide treated with silicone | 1.7 | 1.7 | 1.7 | 1.7 | 1.7 | 1.7 | 1.7 |
|  | (14) | Red iron oxide treated with silicone | 1.2 | 1.2 | 1.2 | 1.2 | 1.2 | 1.2 | 1.2 |
|  | (15) | Black iron oxide treated with silicone | 0.1 | 0.1 | 0.1 | 0.1 | 0.1 | 0.1 | 0.1 |
|  | (16) | Dimethyl polysiloxane (6 mm²/s) | 4 | 4 | 4 | 4 | 4 | 4 | 4 |
|  | (17) | Dimethyl polysiloxane (5000 mm²/s) | 0.6 | 0.6 | 0.6 | 0.6 | 0.6 | 0.6 | 0.6 |
|  | (18) | Squarlane | 2.4 | 2.4 | 2.4 | 2.4 | 2.4 | 2.4 | 2.4 |
|  | (19) | Octyl methoxycinnamate | 3 | 3 | 3 | 3 | 3 | 3 | 3 |
|  | (20) | Antiseptics | Proper amount | Proper amount | Proper amount | Proper amount | Proper amount | Proper amount | Proper amount |
|  | (21) | Perfume | Minute amount | Minute amount | Minute amount | Minute amount | Minute amount | Minute amount | Minute amount |
| Evaluation of use | Adhesion on skin(adhesion) |  | ◉ | ○ | ◉ | ○ | X | X | X |
|  | Extensibility on skin(extension) |  | ◉ | ◉ | ◉ | ◉ | Δ | X | Δ |
|  | Application feeling |  | ◉ | ◉ | ◉ | ◉ | X | X | Δ |
|  | Covering power |  | ◉ | ◉ | ◉ | ◉ | Δ | Δ | X |
|  | Transparency |  | ◉ | ◉ | ○ | ◉ | X | X | Δ |
|  | Non-uneven makeup |  | ◉ | ◉ | ◉ | ◉ | X | X | X |
|  | Fine texture finish |  | ◉ | ◉ | ◉ | ◉ | X | X | X |
|  | Retention of makeup after time lapse(4 hours) |  | ○ | ○ | ○ | ◉ | Δ | Δ | Δ |

◉: evaluated as good by 8 or more panelists
○: evaluated as good by 5 to 7 panelists
Δ: evaluated as good by 2 to 4 panelists
X: evaluated as good by only one or no panelist
*[1]talc: mean particle diameter 10 μm, made by Yamaguchi Mica Co.

The invention claimed is:

1. A cosmetic composition comprising:

(a) composite particles comprising base particles A and fine particles B, wherein the fine particles B have a mean particle diameter of ⅕ or less of the mean particle diameter of the base particles A and the fine particles B are dispersed on the surface of the base particles A, and wherein particle A and particle B are covered with at least one polymer compound selected from the group consisting of a fluorinated polymer compound, dimethyl siloxane•methyl (polyoxyethylene) siloxane copolymer, dimethyl siloxane methyl (polyoxypropylene) siloxane copolymer, polyether-modified silicone, methystyryl-modified silicone, alkyl-modified silicone, fluorine-modified silicone, a higher fatty acid ester-modified silicone, higher alcohol-modified silicone, silicone-modified acrylic resin and a silicone polymer compound including poly(N-acylalkyleneimine) molecular chains having repeating units represented by the formula (III):

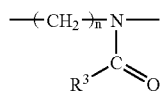
(III)

(in the formula, $R^3$ represents a hydrogen atom, an alkyl group with a carbon number of 1 to 22, a cyloalkyl group with a carbon number of 3 to 8, an aralkyl group with a carbon number of 7 to 10, or an aryl group with a carbon number of 6 to 10, and n represents 2 or 3), bonded to the terminals and/or side chains via the groups represented by the formula (I):

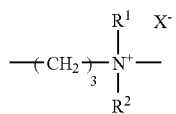
(I)

(in the formula, $R^1$ and $R^2$ independently represent a hydrogen atom, an alkyl group with a carbon number of 1 to 18, or an aryl group with a carbon number of 6 to 10, and $X^-$ represents a counter-ion of a quaternary ammonium ion such as halogen ions such as $Cl^-$ or $Br^-$, or sulfonic acid ester ions such as $CH_3SO_4^-$ and $CH_3CH_2SO_4^-$), or represented by the formula (II):

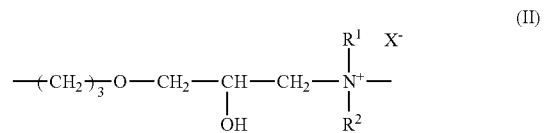
(II)

(in the formula, $R^1$, $R^2$ and $X^-$ represent the same meanings, as described above), said composite particles being obtainable by allowing at least two kinds of particles having different shapes and particle diameters including particles A and B to contact the at least one polymer compound in the presence of supercritical carbon dioxide, and (b) a cosmetic component.

2. The cosmetic composition according to claim 1, wherein the base particles A are flaky particles and the fine particles B are spherical particles.

3. The cosmetic composition according to claim 1, wherein the at least one polymer compound is selected from the group consisting of the fluorinated polymer compound and the silicon polymer compound including poly (N-acylalkyleneimine) molecular chains having repeating units represented by the formula (III).

4. The cosmetic composition according to claim 1 or 2, wherein the cosmetic component (b) comprises at least one spherical powder having a mean particle diameter of 0.001 to 30 μm.

5. The cosmetic composition according to claim 1 or 2, wherein the cosmetic component (b) comprises a powder having a pearlescent shade.

6. The cosmetic composition according to claim 1 or 2, wherein the cosmetic component (h) comprises at least one volatile oil.

7. The cosmetic composition according to claim 1 or 2, wherein the cosmetic component comprises at least one water-soluble thickener.

8. The cosmetic composition according to claim 1 or 2, wherein the cosmetic component (b) comprises zinc oxide with a specific surface area of 10 to 100 m²/g.

9. The cosmetic composition according to claim 1 or 2, wherein the cosmetic component (b) comprises a powder having flaky multi-coated layers wherein at least two metal oxides are sequentially coated on a flaky base material.

* * * * *